(12) United States Patent
Bodlaender et al.

(10) Patent No.: US 8,620,434 B2
(45) Date of Patent: Dec. 31, 2013

(54) METHOD AND SYSTEM FOR DYNAMIC RECALIBRATION OF TENS STIMULATION POINTS TO COMPENSATE FOR CHANGING ELECTRODE CONDITIONS WITH FAIL-SAFE AND AUTO-RECOVERY FUNCTIONALITY

(75) Inventors: Maarten Peter Bodlaender, Eindhoven (NL); Alexander Franciscus Kolen, Eindhoven (NL); Johannes Johanna Van Herk, Valkenswaard (NL); Mirelva M. Drost, Eindhoven (NL); Femke Wagemakers, Eindoven (NL)

(73) Assignee: Koninklijke Philips N.V., Eindhoven (NL)

( * ) Notice: Subject to any disclaimer, the term of this patent is extended or adjusted under 35 U.S.C. 154(b) by 321 days.

(21) Appl. No.: 12/992,110

(22) PCT Filed: May 14, 2009

(86) PCT No.: PCT/IB2009/051996
§ 371 (c)(1),
(2), (4) Date: Nov. 11, 2010

(87) PCT Pub. No.: WO2009/138961
PCT Pub. Date: Nov. 19, 2009

(65) Prior Publication Data
US 2011/0066209 A1 Mar. 17, 2011

(30) Foreign Application Priority Data

May 16, 2008 (EP) .................................... 08156380
Nov. 17, 2008 (EP) .................................... 08169228

(51) Int. Cl.
*A61N 1/32* (2006.01)

(52) U.S. Cl.
USPC ........................................................ 607/45

(58) Field of Classification Search
USPC ............................ 607/116, 148, 152, 45–46
See application file for complete search history.

(56) References Cited

U.S. PATENT DOCUMENTS

| 4,917,093 | A | 4/1990 | Dufresne et al. |
| 8,014,877 | B2 * | 9/2011 | Colthurst ..................... 607/150 |
| 2005/0187591 | A1 | 8/2005 | Carter et al. |
| 2007/0106342 | A1 | 5/2007 | Schumann |
| 2007/0293917 | A1 | 12/2007 | Thompson et al. |
| 2008/0097530 | A1 | 4/2008 | Muccio et al. |

FOREIGN PATENT DOCUMENTS

| EP | 0784960 A1 | 7/1997 |
| WO | 9952588 A1 | 10/1999 |
| WO | 0151122 A1 | 7/2001 |
| WO | 03082104 A1 | 10/2003 |

OTHER PUBLICATIONS

International Search Report—PCT/IB2009/051996.

* cited by examiner

*Primary Examiner* — Amanda Patton

(57) ABSTRACT

A device and method for applying transcutaneous electrical nerve stimulation via an electrode. The device includes the electrode being arranged for detecting a change of a skin impedance and being configured for switching from a stimulation mode of operation for stimulating the nerve, into a recalibration mode of operation upon detection of the changed skin impedance. The device may include a plurality of electrodes being configured for detecting the change of the skin impedance and being configured for adjusting an electrical current flowing through the skin via the plurality of electrodes.

15 Claims, 7 Drawing Sheets

METHOD AND SYSTEM FOR DYNAMIC RECALIBRATION OF TENS STIMULATION POINTS TO COMPENSATE FOR CHANGING ELECTRODE CONDITIONS WITH FAIL-SAFE AND AUTO-RECOVERY FUNCTIONALITY

FIELD OF THE INVENTION

The invention relates to a device and method for trans cutaneous electrical nerve stimulation (TENS).

BACKGROUND OF THE INVENTION

Transcutaneous Electrical Nerve Stimulation (TENS; see also FIG. 1) is a commonly used forms of electroanalgesia (electrical pain relief). Hundreds of clinical reports exist concerning the use of TENS for many types of conditions such as low-back pain, myofascial and arthritic pain, sympathetically mediated pain, bladder incontinence, neurogenic pain, visceral pain and post-surgical pain. TENS is the application of electrical stimulation at the surface of the skin (=transcutaneous), primarily for pain relief. TENS is applied via external surface electrodes with some sort of electrical waveform characterized by frequency, pulse duration and amplitude. The technique of applying electricity for relieving pain well established but gained substantial scientific interest after 1965 after a scientific base was established on the mechanism of pain reduction. TENS is drug-free, noninvasive, and non-addictive. It has hardly any contraindications.

A disadvantage of known TENS devices and methods is that these do not deal with fluctuations in skin conductivity due to for instance movement, moisture build-up or changing temperatures. In known systems this may have the following consequences In case of very poor connection between skin and electrode, stimulation can cause voltage to rise significantly=>potentially undesirable, painful experience.

an inconvenient or cumbersome fail-safe mechanism in case of frequent changes of resistance levels. If the device enters the fail-safe state, the user needs to restart the device frequently. This is not user-friendly.

an earlier selected stimulation point might no longer be the right point

SUMMARY OF THE INVENTION

Amongst others it is an object of the invention to create a TENS device that is suitable for use in contexts where the conductivity between skin and electrode fluctuates over time To this end the invention provides a device as claimed in claim 1 and a method a claimed in claim 14.

A first aspect of the invention comprises a device for applying transcutaneous electrical nerve stimulation via an electrode, the electrode being arranged for detecting a change of skin impedance and being configured for switching from a stimulation mode of operation for stimulating the nerve into a recalibration mode of operation upon detection of the changed skin impedance.

An effect of the device according to the invention is that upon detection of a change of the skin impedance, the device alters its mode of operation from the stimulation mode of operation to a recalibration mode of operation. During the recalibration mode of operation the position of the electrode or the chosen electrode for providing the nerve stimulation signal to the skin from a plurality of electrodes may be altered. As such, the device may, for example, measure the impedance during the recalibration mode and switch to the stimulation mode of operation as soon as the skin impedance is again below, for example, a predefined threshold. As such, the switching into the recalibration mode of operation during a change of conductivity between the skin and the electrode enables a relatively quick return to the stimulation mode of operation and as such enables only a relatively short interruption of the pain suppression when a change in conductivity between the skin and the electrode is registered. As such, the comfort of use of the device is significantly improved.

Known TENS-devices have a so called "fail-safe" mechanism which stops the device when the contact between the electrode and the skin might be broken. If such an interruption happens, the user typically has to restart the device which becomes cumbersome and irritating. Furthermore, the "fail-safe" mechanism does not react to shifting of the electrode from one position on the skin to another. When the electrode shifts without breaking the contact with the skin, the electrode may be at a sub-optimal location which may reduce the effective pain reduction and may even induce pain.

In the device according to the invention, the recalibration mode is entered when a change in skin impedance is detected. This change of skin impedance may be due to a shifting of the electrode to a less optimal position or may be due to bad contact between the electrode and the skin, for example, due to movement. In the recalibration mode, the signal applied by the electrode to the skin is typically lower and is used to measure, for example, the impedance of the electrode or of the plurality of electrodes. When reapplying the electrode or when returning the electrode to the preferred position, the return of the impedance to the original value is detected and the device may directly return to the stimulation mode of operation reapplying pain suppression.

In an embodiment of the device, the device comprises a plurality of electrodes being configured for detecting the change of the skin impedance and being configured for adjusting an electrical current flowing through the skin via the plurality of electrodes. Using an array of electrodes enables a relatively simple switch over from a first electrode used for the stimulation signal to a second electrode which will be used for the stimulation signal.

In an embodiment of the device, the changed skin impedance results in a failure in the functioning of the device.

In an embodiment of the device, the device is configured for providing the transcutaneous electrical nerve stimulation simultaneously via more than one electrode, and wherein the device is configured for varying the voltage per electrode for applying the transcutaneous electrical nerve stimulation. A benefit of the use of a plurality of electrodes simultaneously is that it enables to reduce the impedance between the skin and the plurality of electrodes, and that the area over which the stimulation is received may be increased. A further advantageous embodiment comprises an array of electrodes in which the electrodes have relatively small dimensions. Dimensions at or below 1×1 millimeters enables to select a number of electrodes which relatively closely cover the area on the skin having relatively low impedance. This may relatively easily be done via known semiconductor manufacturing techniques in which the sub-millimeter electrodes may be produced. Even more preferably the dimensions of the electrodes may be at or below 0.5×0.5 millimeters which enables to even more closely cover the area on the skin with relatively low impedance.

When the voltage per electrode is varied for applying the transcutaneous electrical nerve stimulation, the signal used to provide the transcutaneous electrical nerve stimulation may be adapted for each of the electrodes, thus optimizing the electrode due to, for example, local impedance variations. As such, the current provided to the skin may be homogeneously distributed over all of the electrodes used to provide the transcutaneous electrical nerve stimulation.

In an embodiment of the device, the device is configured for converting a variation of the voltage for applying the transcutaneous electrical nerve stimulation in response to the changed skin impedance into a variation in the number of electrodes for providing the transcutaneous electrical nerve stimulation. Changes in desired voltage for providing the transcutaneous electrical nerve stimulation are translated into changes in the number of electrodes (and thus changes in resistance) that are used to stimulate the skin. This embodiment gives the physician more control in the area of stimulation, specifically, it allows for very small areas of stimulation, which means the voltage is near its maximum. Therefore, if the user then wants to increase the current, the voltage can not be further increased and thus the number of electrodes via which the increased current is supplied to the skin may be increased instead.

In an embodiment of the device, the stimulation mode of operation comprises a stimulation-voltage and wherein the recalibration mode of operation comprises a measuring-voltage, the measuring-voltage being lower than the stimulation-voltage. For measuring the impedance at the location of the electrodes, typically less strong signal is required. To reduce the signal during the recalibration mode of operation, the overall energy consumed by the device is reduced. Furthermore, the reduction of the signal strength improves the convenience of a patient during the recalibration mode of operation. When the contact between the electrode and the skin is not optimal, relatively large voltages may occur causing a relatively painful experience to the patient. This is prevented by reducing the signal strength during the recalibration mode of operation.

In an embodiment of the device, the device is configured for detecting a changed skin impedance via monitoring a voltage required for applying the transcutaneous electrical nerve stimulation at substantially constant current, and/or via monitoring a current resulting from applying the transcutaneous electrical nerve stimulation at substantially constant voltage, and/or via measuring a resistance of the electrode. The monitoring of the stimulation-voltage enables the detecting of a change in impedance while applying the transcutaneous electrical nerve stimulation. As such, the detection of the change in skin impedance does not require an interruption of the applying of the transcutaneous electrical nerve stimulation. The electrodes which are not used for nerve stimulation may be measured via a resistance measurement method which typically requires less power.

In an embodiment of the device comprising the plurality of electrodes, the device is configured for measuring of the resistance of the electrodes one by one, or in groups. The group may, for example, be set of electrodes that previously already had a relatively low resistance and as such may relatively quickly lead to a new electrode from the plurality of electrodes for providing the transcutaneous electrical nerve stimulation signal.

In an embodiment of the device comprising the plurality of electrodes, the device is configured for detecting the change of the skin impedance during the stimulation mode of operation, the resistance of a stimulation electrode from the plurality of electrodes being measured via monitoring the voltage for applying the transcutaneous electrical nerve stimulation, and wherein the device (10, 12, 14) is configured for detecting the resistance of a non-stimulation electrode (22) from the plurality of electrodes (18) via the measuring-voltage measuring the resistance of the electrode (22), the stimulation electrode (22) being configured for applying the transcutaneous electrical nerve stimulation, and the non-stimulation electrode (22) being configured for not applying the transcutaneous electrical nerve stimulation. During the active stimulation, voltage measurement is used to detect when the stimulation electrode(s) are no longer suitable for providing the transcutaneous electrical nerve stimulation. It might be that due to connection recovery of one of the other electrodes, that other electrode becomes suitable for stimulation. To benefit from such possible recoveries, it is preferred to measure the resistance also for electrodes that are not being stimulated. As soon as the current electrode is no longer suitable, a next electrode may be chosen from the resistance measurements which have been done. Therefore, during the stimulation phase resistance measurements on the stimulation electrode use a high-voltage measurement method. Due to the high voltages and the typically short stimulation pulses, the precision of this measurement method is comparably low, but the measurement suffices for fast reactions of the fail-safe mechanism. For the non-stimulation electrodes and for higher precision measurements, the low-voltage measurement method is used. Either all electrodes are measured during such a break or a subset of electrodes is measured in a single break, to keep these breaks limited in time. If during stimulation it is detected that a non-stimulation electrode has a comparable or even lower resistance than the (some of the) stimulation electrode(s), this non-stimulated electrode is added to the set of electrodes that are available for stimulation. It then depends on the actual stimulation strategy whether the new electrode is used for stimulation. For this invention, it is preferred that if the original stimulation electrode(s) lose their good connection to the skin, this newly discovered electrode can then be used to take over stimulation.

In an embodiment of the device, the device is configured for measuring the resistance of the non-stimulation electrodes during short breaks in the applying of the transcutaneous electrical nerve stimulation. As the stimulation would interfere with the low-voltage measurement method, this measurement occurs in short breaks in the stimulation. Furthermore, pulses used during low-voltage measurement are typically longer in duration then pulses used during high-voltage measurement, to ensure that for the capacitor-function of the skin does not decrease the accuracy of the measurement.

In an embodiment of the device comprising the plurality of electrodes, the device is configured for measuring a resistance of the electrodes of the plurality of electrodes for identifying a new stimulation electrode during the recalibration mode of operation.

In an embodiment of the device, the device is configured for measuring the resistance of the electrodes of the plurality of electrodes for a first sub-set of electrodes. This first sub-set may, for example, be a set of electrodes which originally already had a relatively low impedance value between the electrode and the skin and thus may comprise an electrode or a reduced set of electrodes via which the transcutaneous electrical nerve stimulation may be resumed.

In an embodiment of the device, the device is configured for applying a stimulation signal for stimulating the nerve to a second sub-set of electrodes of the plurality of electrodes during a predefined time-window, and for monitoring a resistance change of the electrodes of the second sub-set over time, and wherein the device is configured to select a specific electrode or a specific group of electrodes from the second sub-set in which the resistance change over time is below a predefined limit as the stimulation electrode or stimulation electrodes. Such a pre-stimulation during the predefined time-window may be used to more clearly find a good nerve stimulation electrode. This pre-stimulation mechanism initially stimulates all available electrodes from the second sub-set for a limited duration (a maximum of 5 minutes suffices, but after 2.5 minutes the slope of the skin resistance improvement is also clear). This will result in a skin resistance drop for all points. Since resistance typically drops between 25% and a factor of 12, this can result in a different stimulation point having the lowest resistance. Only at this time, select the actual stimulation points, based on a final resistance measurement.

Alternatively, the history of the change in resistance is monitored. This gives an average resistance pre-stimulation and post-stimulation, and a resistance change-speed. On determining a new stimulation point, consider for stimulated electrodes also their pre-stimulation resistance when comparing them with a non-stimulated electrode. If using this second metric a competitive electrode is found (e.g. measured resistance differs less then X %, where X is e.g. 20%), it can be stimulated for a limited duration (2 to 5 minutes) such that also their post-stimulation resistances can be compared. Using the resistance change-speed it can be calculated whether a stimulated electrode has reached its lowest resistance, or whether its resistance is still decreasing. This is important as the time it takes to reach the lowest resistance varies from 2 minutes to 15 minutes depending on person and circumstances. Finally, select the electrode with a competitively low post-stimulation resistance that had a lowest resistance change during the predefined time-window. The reason for this is that it has been identified that good stimulation points typically have a lower resistance improvement then poor stimulation points. The theory behind this is that good stimulation points have a free nerve end or nerve closer to the skin than poor stimulation points, and that stimulation of the skin improves its conductivity. Since for a good point there is less skin-tissue that can improve its conductivity, the improvement from stimulation is necessarily lower.

The second sub-set may be a reduced set from the plurality of electrodes available to the device, for example, on an electrode pad. Alternatively, the second sub-set may be all electrodes from the plurality of electrodes available to the device.

In an embodiment of the device, the device is configured for adjusting the electrical current during the recalibration mode of operation via adapting a location of the electrode or of the plurality of electrodes for reducing the resistance of the electrode or of the plurality of electrodes, and/or via reapplying of the electrode or of the plurality of electrodes for reducing a resistance of the electrode or of the electrodes. For example, due to moving the connection of the electrode to the skin is less good or the electrode has moved. Often, the stimulation point may be found relatively easily as a red coloring of the skin is visible at the original stimulation point. It would take only little effort to instruct the patient or therapist to move the electrode to its original location, for example, upon a signal or upon instructions from the device.

The device may also be configured for adjusting the electrical current during the recalibration mode of operation via selecting a further electrode having reduced resistance from the plurality of electrodes for applying the transcutaneous electrical nerve stimulation. Choosing a different electrode having reduced resistance also adjusts the electrical current flowing through the skin, both in location and in amplitude.

The device may also be configured for adjusting the electrical current during the recalibration mode of operation via selecting a third sub-set of electrodes from the plurality of electrodes for applying the transcutaneous electrical nerve stimulation simultaneously via the electrodes of the third sub-set of electrodes for reducing the resistance of the electrode or of the plurality of electrodes. Selecting a plurality of electrodes enables to relatively easily reduce the impedance as the overall impedance of two parallel arranged impedances is lower than any of the impedances individually. Furthermore, such an embodiment enables to follow the local anatomy thus improving stimulation effectiveness.

The device may also be configured for adjusting the electrical current during the recalibration mode of operation via selecting a fourth sub-set of electrodes from the plurality of electrodes for applying the transcutaneous electrical nerve stimulation, wherein the fourth sub-set of electrodes is chosen depending on local physiology, sensed resistance and user interaction. The user may be able to alter the size of the fourth sub-set of electrodes via which the transcutaneous electrical nerve stimulation is applied. Alternatively, local physiology determines the size of the fourth sub-set of electrodes to ensure efficient stimulation by the device.

In an embodiment of the device when adapting a location and/or re-applying the electrode or the plurality of electrodes, the device is configured for providing instructions to a user for adapting the location and/or reapplying the electrode or the plurality of electrodes. When, for example, measurement history of a number of electrodes is maintained, it may be possible to redirect the patient or the therapist to move the electrode or the plurality of electrodes in a direction where previously relatively low impedance was measured. It may also be possible to extend on this by looking for pre-defined patterns in received measurements, especially when using an array of a plurality of electrodes. The instructions may include user notifications like "move electrode further down" or "check skin contact".

In an embodiment of the device wherein the device is configured for selecting a further electrode having reduced resistance from the plurality of electrodes, the plurality of electrodes are arranged on an electrode pad.

A second aspect of the invention comprises a method of transcutaneous electrical nerve stimulation comprising the use of a device comprising an electrode whereby the method comprises the step of:

detecting a change of a skin impedance, and switching from a stimulation mode of operation (30) for stimulating the nerve into a recalibration mode of operation (32) upon detection of the changed skin impedance.

In an embodiment of the method, the method further comprises the step of dynamically adapting the number of electrodes used for stimulation by adding neighboring electrodes to an existing stimulation electrode, the added neighboring electrodes having relatively low impedance. A benefit of this embodiment is that it allows following the local anatomy thus improving stimulation effectiveness.

The method may further comprise the step of dynamically adding neighboring electrodes to an existing stimulation electrode in which the neighboring electrodes having a least distance from the relatively low impedance location. A benefit of this embodiment is that it improves the ability to deal with slight shifts of electrodes such that the lowest resistance point is still stimulated.

The method may further comprise the step of dynamically adding electrodes depending on known physiology of the body part to which the electrode array is applied. A benefit of this embodiment is that it enables homogenous stimulation of larger-sized muscles, glands or nerves.

DESCRIPTION OF THE FIGURES

The above and other objects and features of the present invention will become more apparent from the following detailed description considered in connection with the accompanying drawings [which disclose an embodiment of the present invention in which.

The correct functioning of a TENS device depends for a significant part on whether the electrodes that it uses to connect to the skin make good contact with the skin, and are applied in the right position.

Due to advances in miniaturization of technology and advances in battery life, so-called portable-TENS devices have appeared on the market. These are beneficial for users, as they can offer pain-relief not only in a static context like in a hospital, but in a variety of places, like at home, at work or on the move (see for example FIG. 3). Especially for such portable TENS devices, the contact between the electrodes and the skin is hard to maintain, due to moments of the body and the varying environment conditions.

Figure 3:
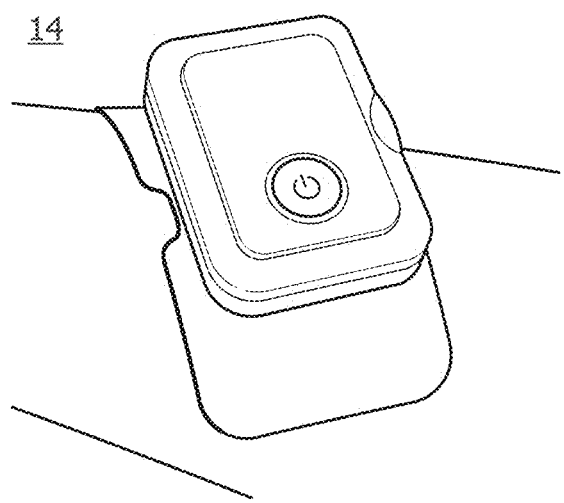
FIG. 3 shows a portable TENS device.

FIG. 3 A Portable TENS Device

Figure 1:
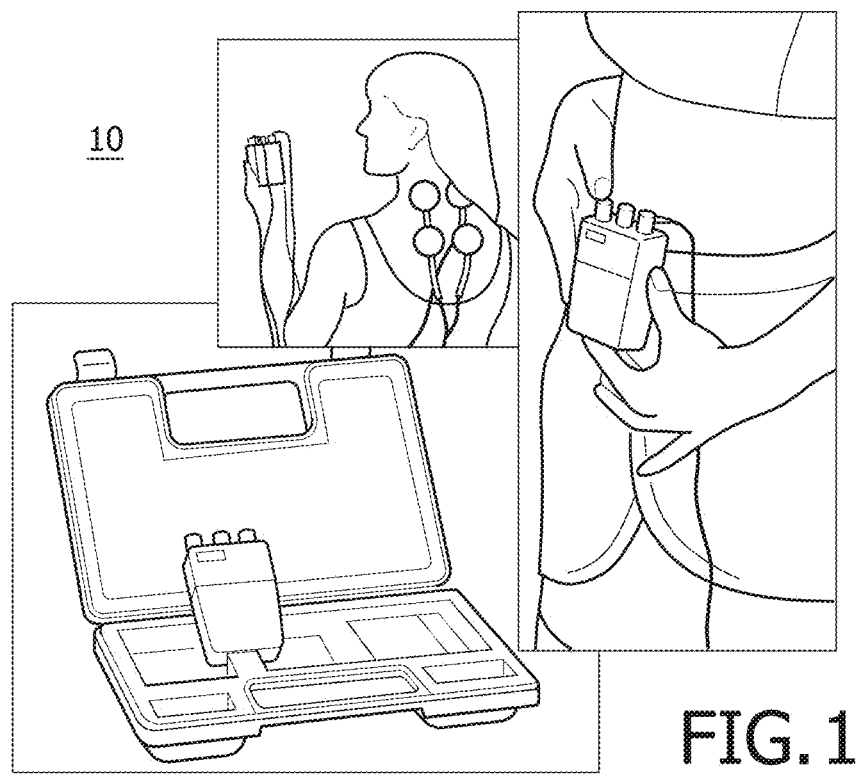
FIG. 1 shows an example of a known TENS device.
Figure 2:
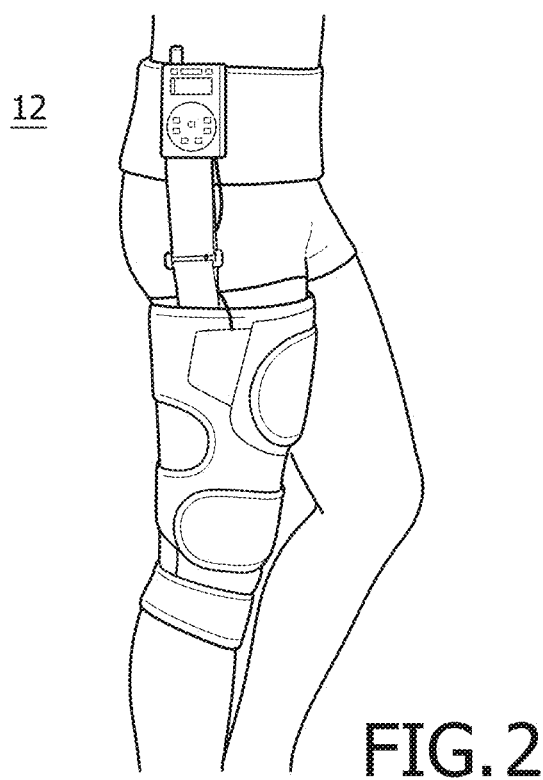
FIG. 2 shows example of brace/electrode combination.

Typically, electrodes are held in place using glue (see for example FIG. 1), using a brace or garment that presses the electrodes to the skin, or using a combination of both (see for example FIG. 2). A known disadvantage of glue is that prolonged use often irritates the skin; therefore more and more dry-electrode solutions are being developed. A second disadvantage is that electrodes based on glue or gels lose part of their adhesive strength after a limited number of uses.

Applying the electrode to the right position is difficult for device users that are not experts. WO1999052588A1 describes a constellation of electrodes (like a matrix) that automatically finds the right stimulation point using resistance measurements. It is possible to extend on this by looking for pre-defined patterns in received measurements, and it includes user notifications like "move electrode further down" or "check skin contact". Together, these inventions provide a significant benefit to the user by selecting the right stimulation point.

Figure 4:
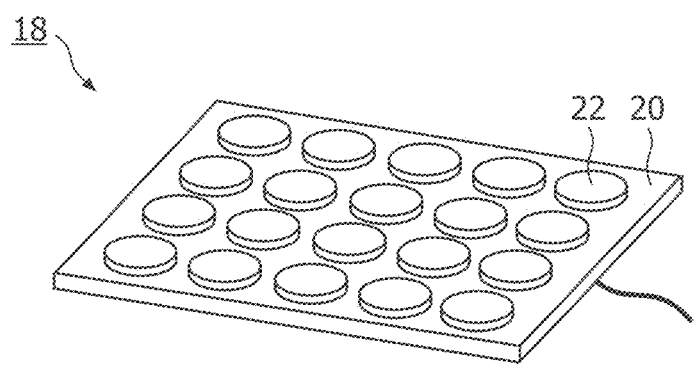
FIG. 4 shows protruding electrodes.

Another way to improve the contact between electrodes and skin is to use protruding electrodes, WO03/082104A1, see FIG. 4.

FIG. 4 Protruding Electrodes

None of the mechanisms presented above can fully ensure that the contact between the electrode and the skin is not sometimes disturbed (by accident). For example, the glue that is used to secure electrode is typically such that the electrode can be easily removed after use, and this places limits to its adhesive character. Braces and garments have the tendency to shift their position on the skin and they can deform, losing connection between the electrode and the skin. While protruding electrodes improve skin contact, they cannot guarantee it.

Several TENS devices have a FAIL-SAFE auto-shutoff mechanism, that stops the stimulation if the contact between electrode and skin is lost. This prevents potentially dangerous or unpleasant shocks to users that can occur from accidental touching of dangling electrodes. Once the device has shutoff, it takes a user command to restart the stimulation.

There are significant disadvantages to the known FAIL-SAFE mechanism. First, in a dynamic environment, the contact between the electrode and the skin might quite frequently be broken and the FAIL-SAFE mechanism frequently stops the device. In this case, the user has to restart the device frequently, an action that becomes cumbersome and irritating. In addition, if the user forgets or is not able to restart the device, the device no longer suppresses pain. Secondly, the known FAIL-SAFE mechanism does not react to shifting of the electrode from one position on the skin to another. In this case, while the skin contact is not broken, it might be that a sub-optimal location is now stimulated, which reduces the effective pain reduction and can even induce pain.

EMBODIMENT 1

Auto Recovery from Poor Connections Between Skin and Electrode

The functioning of the TENS device can be described by a state machine. When the device is actively stimulating the skin through the electrodes, it applies high voltages (of approximately 80 to 160 volts for 0.3 milliseconds) to the skin. This is called the HIGH-VOLTAGE STIMULATION state.

The stimulation mechanism typically uses a constant current I. Since the resistance R of the connection between the electrode and the skin varies, the stimulation mechanism adapts the voltage dynamically to keep the current constant:

$$R = V/I$$

If the voltage exceeds a predefined voltage level $V^{maxstim}$ (due to an increasing resistance level I) as a fail-safe mechanism, the device stops the high voltage stimulation.

Whereas a traditional TENS fail-safe mechanism would now enter a stop-state, the invented TENS device switches instead to the LOW-VOLTAGE MEASURING state. In this state, there is no stimulation applied to the skin, but a low-voltage current (typically between 1 and 10 volts) is applied to a subset of the electrodes, while the current I is no longer kept constant but allowed to range between 0 and $I^{maxstim}$. A separate electrical circuit (possibly embedded in a (reconfigurable) high-power chip) is preferred to implement this.

If the device has a plurality of electrodes, it is possible to measure the resistance at these electrodes one by one, or in groups at the same time. Specifically it is beneficial to measure a set of electrodes that previously all had high resistance all at the same time. If high resistance for the entire set is measured, all electrodes are classified as having high resistance. If a low resistance is measured for the group, further measuring subsets this group can determine which electrodes have the lowest resistance.

Resistance Measurement of Electrodes Classifies the Electrodes in Three Sets.

The LOW-RESISTANCE SET is the set of electrodes with sufficiently $V^{maxstim}$ low resistance to stimulate without exceeding $V^{maxstim}$. If this set is no longer empty, the device auto-recovers and reverts to the HIGH-VOLTAGE STIMULATION state.

The MED-RESISTANCE SET is the set of electrodes that have an resistance such that active stimulation would cause the voltage to exceed $V^{maxstim}$, but the resistance is below a second cut off level $R^{max}$. Electrodes in this set connect to the skin, with an insufficiently low resistance to stimulate them.

The HIGH-RESISTANCE SET is the set of electrodes with the highest resistances, above second cut off level $R^{max}$. Electrodes in this set are no longer assumed to be connected to the skin, and should thus not be used for stimulation.

If resistance measurements classify all electrodes as high-resistance electrodes, the electrode-patch might be removed from the skin in its entirety. After a limited duration in which further measurements are conducted, the device enters the STOP state if all further measurements measured classified all electrodes as high-resistance electrodes.

In the STOP state, the device does not measure resistance and does not stimulate. A user action is needed to restart stimulation.

Figure 5:
FIG. 5 shows an overview of the states of a TENS device according to the invention.

FIG. 5 provides an overview of the three classifications in case of a single electrode (and ground), and how the device reacts to the measured resistance.

Fail-safe stimulation system with three states and two resistance measurement methods.

SM stands for Stimulation mode. If the device a resistance-level below threshold T11, the device starts stimulation, including high-voltage measurement of resistance.

RM stands for recalibration mode which is a kind of auto-recovery. If the device measures a resistance-level above threshold T11, the device directly stops stimulation but starts low-voltage measurement of resistance.

FS stands for Fail-Safe. If the device measures a resistance-level above threshold T12 for a certain duration, the device stops stimulation and stops measuring resistance, and will only restart on explicit user command.

Figure 6:
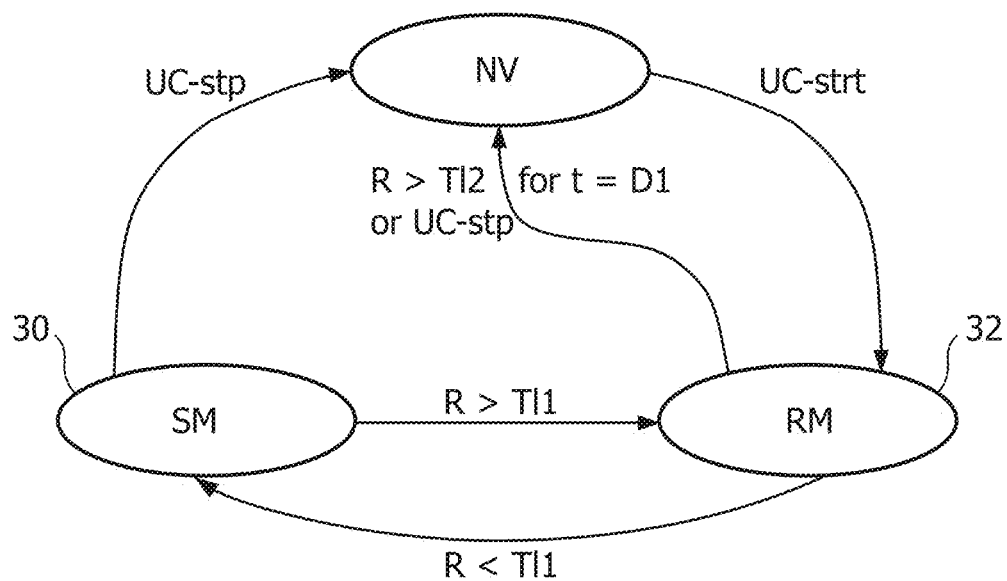
FIG. 6 shows a summary of basic fail safe with auto-recovery mechanism of a TENS device according to the invention.

FIG. 6 shows the state transition diagram that summarises the basic fail safe with auto recovery mechanism.

NV=No-voltage stop state
SM=high voltage stimulation state, and
RM=recalibration mode and stands for low-voltage measuring state
R>T11=resistance above threshold T11,
R<T11=resistance below threshold T11,
R>T12 for t=D1=resistance above T12 for duration D1
UC-stp=User Command Stop
UC-strt=User Command Start Initially, the device is in the stop state NV, and does not apply any voltage to its electrodes. If the user gives a command to start stimulation UC-strt, as a first step the device measures whether an electrode is available for stimulation in the measuring state RM, using low voltages. If no such electrode is detected, and a too high resistance is found, after a timeout D1 the device shuts off, going back to the stop-state NV. If on the other hand a electrode is found that has a low enough resistance (R<T11), the device enters the stimulation state SM. It will then apply higher voltages to the electrode, to stimulate the user. During this stimulation, the resistance on the stimulation electrode(s) is measured by means of monitoring the actual voltage. If the resistance becomes too high (R>T11) for effective stimulation, the device stops stimulation, and goes back to the measuring state RM.

User notification #1: The device tracks how long it has been in the low-voltage measuring state, and it notifies the user after a certain period of time USERTIMER1 that no suitable stimulation point is found. Also when the device enters the stop state due to the auto-shutoff mechanism (As opposed to due to a user command), the device communicates this to the user. In this case, the user will need to improve the contact between the electrode and the skin. (see also the electrode patterns patent filing).

User notification #2: It is also possible that the device sporadically enters the stimulation state for a brief time, but that it primarily is in the measuring state. In this case, the effective stimulation duration is short, but the previous mechanism will not notify the user as USERTIMER1 is not reached. It would be advantageous if a user would be notified of a poor connection if the actual stimulation time falls below X % in a certain interval USERTIMER2. Therefore, the device tracks for the last USERTIMER2 time how much time it is in the stimulation phase: STIM %. If STIM %<X %, the user is notified.

A straightforward way of maintaining STIM % is to maintain a queue in memory (time, stimevent), where stimevent is start or stop. In addition, the sum of all closed [stimstart, stimend] intervals that fully falls within [timenow−USERTIMER2, timenow] is maintained: STIMTOTAL1, with the exception that if for >USERTIMER2 time stimulation has been ongoing, STIMTOTAL1 is set to USERTIMER2.

To calculate the total stimulation time in interval [timenow−USERTIMER2, timenow], the following simple algorithm is used:

STIMTOTAL=STIMTOTAL1 (include all closed intervals)

STIMTOTAL+=$t$−(timenow−USERTIMER2), if (t,stimend) is the oldest event in the queue. (include the oldest, open interval)

STIMTOTAL+=timenow−$t$, if (t,stimstart) is the newest event in the queue (include the newest, open interval)

STIM % is now STIMTOTAL/USERTIMER2.

The following steps are taken to maintain this queue: if for last event in queue (t, event) it holds that t<time-now-USERTIMER2, remove (t, event) from queue.

If event=stimstart and queue is not empty, next event is (t2, stimend) STIMTOTAL1−=(t2−t) (stimtotal1 maintains only the closed intervals, note)

If event=stimstart and queue is now empty, STIMTOTAL1=USERTIMER2 (exception when stimulation has been ongoing for at least USERTIMER2 time, we define STIMTOTAL1 as USERTIMER2)

If the device switches from measuring state to stimulation state, add (timenow, stimstart) to queue If the device switches from stimulation state to measuring state, add (timenow, stimend) to queue.

If there is a previous event (t,stimstart) on queue: STIM-TOTAL1+=(timenow−t)

Else, STIMTOTAL1=0 (queue was empty)

The disadvantage of this straightforward implementation is that it places no bound on the size of the queue, which can be problematic for an small portable device. To simplify the implementation of maintaining STIM %, an approximation of STIM % can be maintained instead.

A simple approximation of STIM % is by maintaining two variables, stim1 and stim2.

They are defined as follows:

Stim1 contains the actual stimulation time in the interval [timenow, P] where P is defined as follows:

$P = \text{Timenow} - \text{Timenow modulo} 2*\text{USERTIMER2}$

Figure 7:
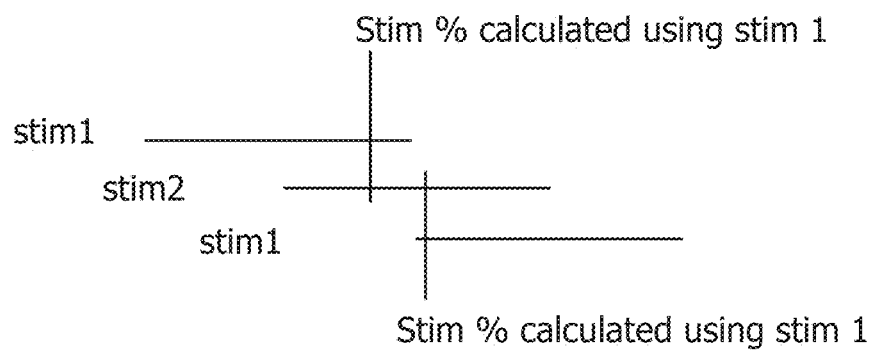
FIG. 7 shows stimuli tracks with overlapping intervals of stimulation time.

Stim2 contains the actual stimulation time in interval [timenow, Q], where Q is defined as follows:

$Q = \text{Timenow} - (\text{Timenow} + \text{USERTIMER2}) \text{ modulo} 2*\text{USERTIMER2}$ The effect is shown in FIG. 7. Stim1 and Stim2 basically "reset" periodically to 0, with two overlapping periods. Therefore at any time, one of the variables has accurately tracked at least how much stimulation has occurred for USERTIMER2 time.

A good estimate that can be made from these two variables of how much stimulation has occurred in the last USERTIMER period is the following:

Define stim1duration=timenow modulo 2*USERTIMER2
Define stim2duration=(timenow+USERTIMER2) modulo 2*USERTIMER2

Estimation Method:

If stim1duration>stim2duration STIM %=stim1/stim1duration

Else STIM %=stim2/stim2duration

This method ensures that the stimulation percentage is always estimated over a period with a length between USERTIMER2 and 2*USERTIMER2.

The principle can be extended to 3 or more overlapping variables, which will shrink the variance of the length interval over which the stimulation percentage is estimated.

Figure 8:
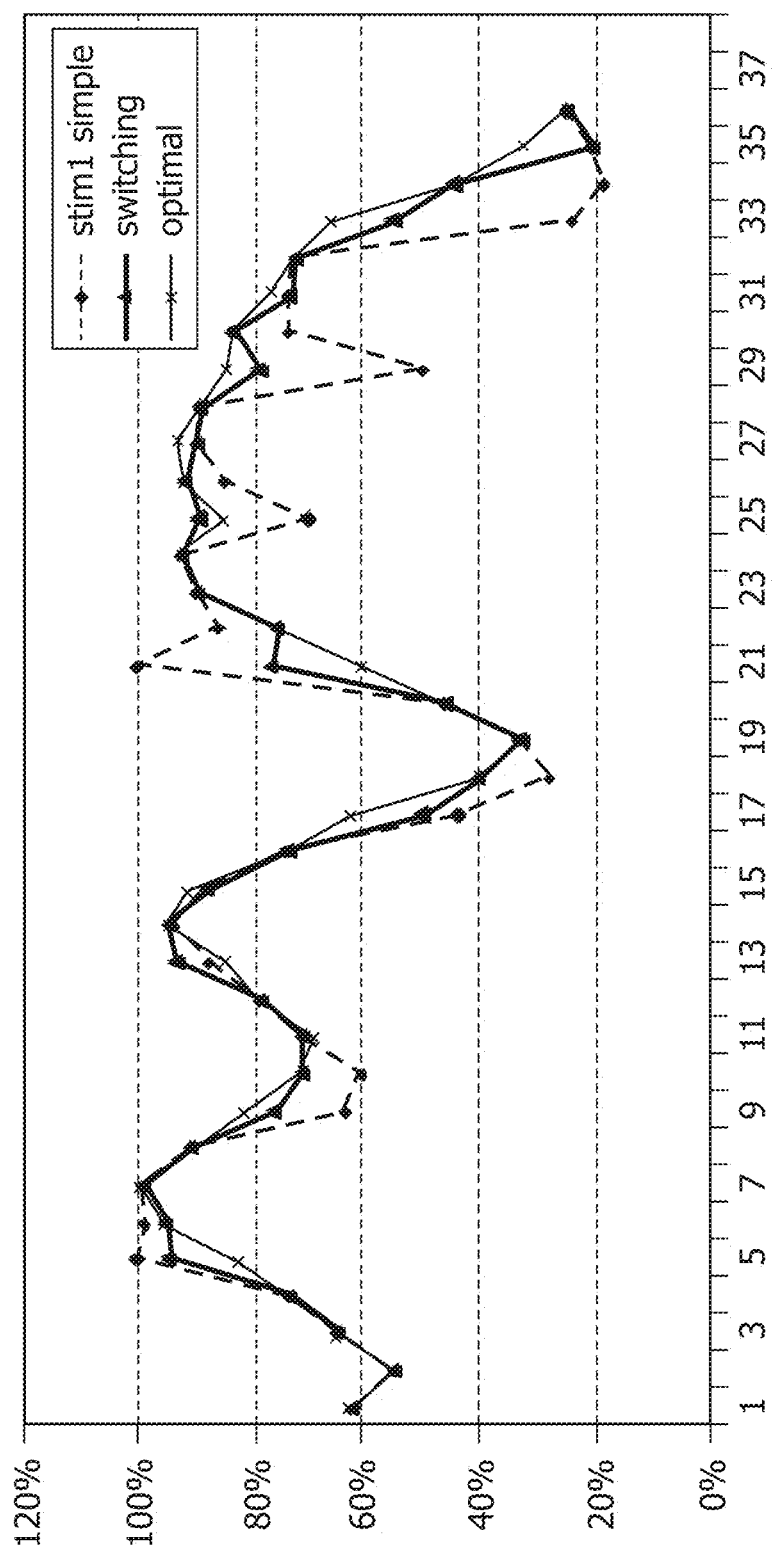
FIG. 8 shows simulation of stimuli estimation using 2 variables versus only 1 variable.
Figure 9:
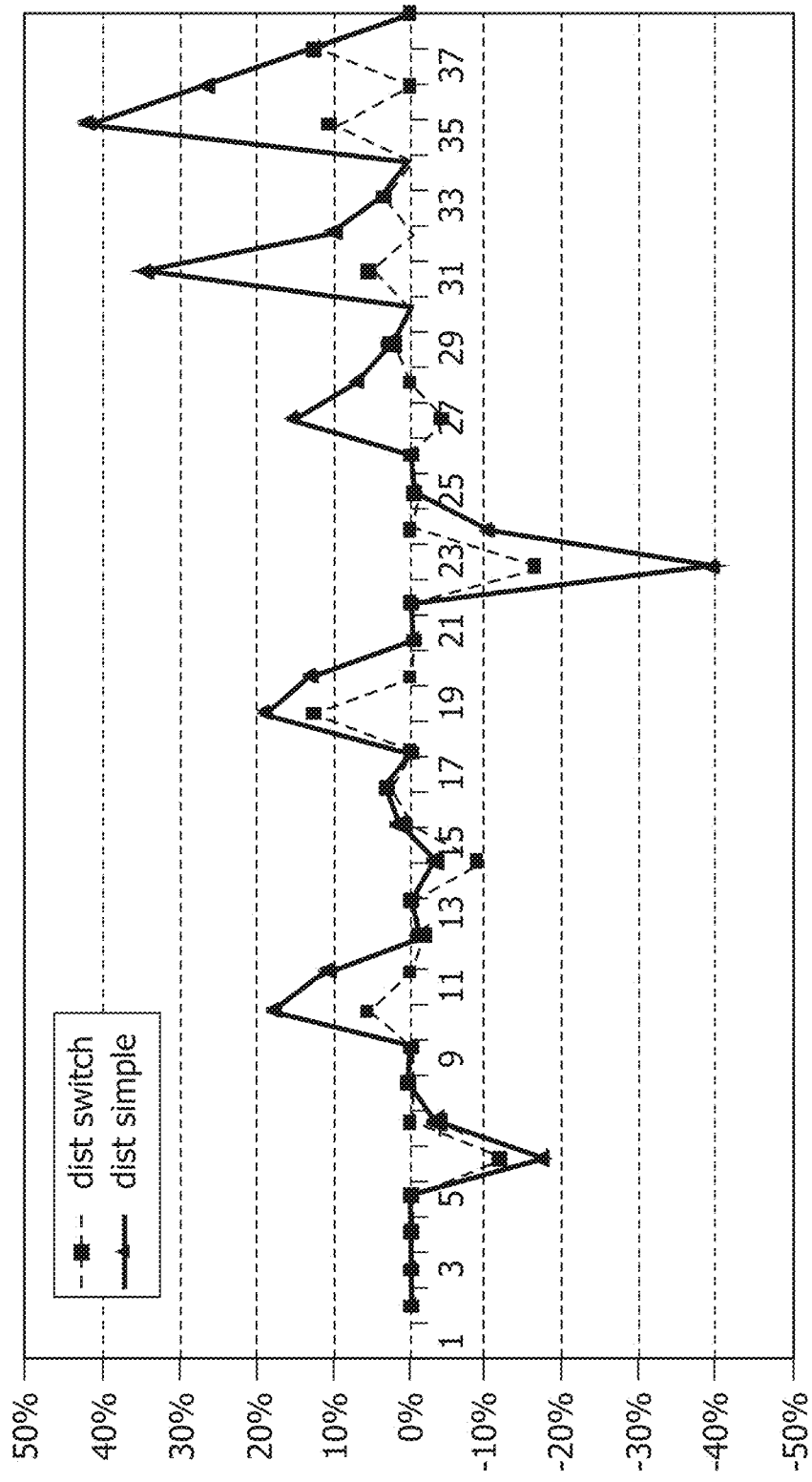
FIG. 9 shows errors in a simulation of using one periodically reset variable versus two periodically reset variables in overlapping periods.
Figure 11:
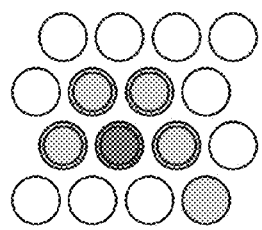
FIG. 11 shows an advantageous geometry with equal distances between stimulation areas.
Figure 12:
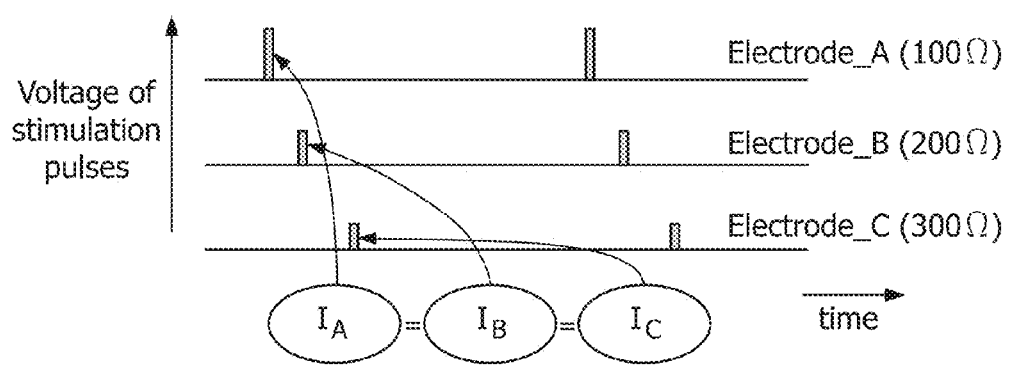
FIG. 12 shows an example with 3 electrodes where each electrode applies the same current, while offering different voltages. In this example, stimulation impulses are slightly shifted in time to simplify keeping within voltage limits of the device, simultaneous stimulation is also feasible.

FIG. 8 shows a simulation of tracking effective stimulation time, and how the estimation with either one or two periodically reset stim-variables differs from the queue-based calculation. FIG. 11 shows that with two stim-variables, differences from the queue-based calculation are much less then with one variable. Furthermore, it can be seen that the switch technique does not continuously over—nor underestimates the actual stim %.

EMBODIMENT 2

Stimulation of Multiple Electrodes in Physical Proximity to Reduce Effect of Changes in Resistance and Shifting Positions on the Skin Electrodes in the MED-RESISTANCE SET should only be used for stimulation if they are used in parallel to at least one electrode in the LOW-RESISTANCE SET. The resulting resistance of the combination is guaranteed to be lower then a single electrode, as follows:

$1/R\text{combined} = 1/R\text{low} + 1/R\text{med}$

The advantage of stimulating multiple electrodes is that if the resistance of the selected stimulation electrode changes (for example goes up significantly); the effect on the combined resistance is lessened by the presence of other electrodes. Other low-resistance or medium-resistance points can be used for additional stimulation points. Advantageously, such additional electrodes should be physically close to the selected stimulation electrode, if the electrodes shift across the skin, the additional electrodes could shift to the lower resistance point. See for example FIG. 10.

Figure 10:
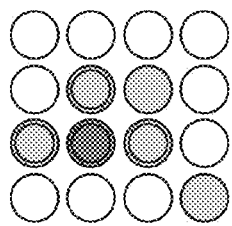
FIG. 10 shows low-resistance points selected for stimulation together with three medium-resistance points that partially surround it. Light gray points have a too high resistance to be suitable for stimulation.

FIG. 10 The (green) low-resistance point is selected for stimulation together with three (dark gray) medium-resistance points that partially surround it. Light gray points have a too high resistance to be suitable for stimulation.

FIG. 11 Advantageous Geometry with Equal Distances Between Stimulation Areas A preferred geometry of multiple electrodes is in a honeycomb structure, with shifted rows. This ensures that distances between electrodes are all equal, making it easier to select additional stimulation points around the low resistance point. See for example FIG. 11.

It is an object of this invention to calculate which area should be actively stimulated.

Three Additional Stimulation Point Selection Mechanisms:

1) Add neighboring point to existing stimulation point with locally lowest resistance (so lower then all other neighboring points)

a. Advantage: follow anatomy thus improving stimulation effectiveness.

2) Add neighboring point with least distance to lowest resistance point & secondary with lowest resistance amongst equidistant neighboring points.

a. Advantage: improves ability to deal with slight shifts of electrodes, lowest resistance point is still stimulated.

3) Stimulation points are selected according to the known physiology of the body part to which the electrode array is applied.

a. Advantage: this enables homogenous stimulation of larger-sized muscles, glands or nerves.

The number of additional stimulation points that is added has a dual influence:

a) It increases the current applied to the body. No more then 50 mA may be applied to the human skin. Therefore, no additional neighboring points can be added if $V = I*R \Rightarrow I = V/R$ As V is maximally 150 volts in our prototype, a safe estimate is $I = 150/R$ The resistance R of the set of stimulation electrodes 1 . . . n is defined by $R = 1/(1/R\_1 + 1/R\_2 + \ldots + 1/R\_n)$ As I<50 mA, an electrode n+1 may still be added if SAFESTIM: 50 mA>150/(1/(1/R_1+1/R_2+ . . . +1/R_n+1_R_(n+1)))

For devices with a different V_max, the formula changes to SAFESTIMv: 50 mA>V_max/(1/(1/R_1+1/R_2+ . . . +1/R_n+1_R_(n+1)))

It should be appreciated that it is advantageous to have an array for electrodes with a small dimension, as this guarantees that the SAFESTIM requirement can always be met with one or more electrodes.

b) It changes the area on the human body that receives stimulation.

While the maximum current is legally bound to 50 mA, the user of the device can between 0 and 50 mA control how much current is applied to the body. The official recommendation for a TENS treatment is that the resulting effect should be "strong yet comfortable". The current-level is subjective, and differs per subject. We propose two mechanisms to control how much current is applied to the skin:

1) The traditional mechanism: increase the voltage, which in turn will increase the current to the skin.

2) A new mechanism, where changes in desired voltage are translated into changes in the number of electrodes (and thus changes in R) that are used to stimulate the skin.

This second mechanism gives the physician more control in the area of stimulation, specifically, it allows for very small areas of stimulation, which means the voltage is near its maximum. Therefore, if the user then wants to increase the current, the first mechanism cannot be used.

The advantage of small stimulation areas is:

a) More targeted stimulation: all energy is applied to the intended area and doesn't dissipate in non-functional tissue.

In the specific application of functional electro stimulation, where the muscles are directly targeted, it can be advantageous to use lower voltages and larger areas, to ensure that entire muscle-groups receive the same stimulation intensity.

Our device is able to vary voltage per electrode, which is advantageous as it allows a homogeneous distribution of current over the different electrodes.

EMBODIMENT 3

Two Measurement Modes in the Stimulation Phase to Benefit from Recovering Electrodes During the active stimulation, voltage measurement is used to detect when the stimulation electrode(s) are no longer suitable for electrodes. It might be that due to connection recovery of one of the other electrodes, that other electrode becomes suitable for stimulation. To benefit from such possible recoveries, it is preferred to measure the resistance also for electrodes that are not being stimulated.

Therefore, during the stimulation phase resistance measurements on the stimulation electrode use the high-voltage measurement method. Due to the high voltages and the typically short stimulation pulses, the precision of this measurement method is comparably low, but the measurement suffices for fast reactions of the fail-safe mechanism. For the non-stimulation electrodes and for higher precision measurements, the low-voltage measurement method is used. As the stimulation would interfere with the low-voltage measurement method, this measurement occurs in short breaks in the stimulation. Either all electrodes are measured during such a break or a subset of electrodes is measured in a single break, to keep these breaks limited in time. Furthermore, pulses used during low-voltage measurement are typically longer in duration then pulses used during high-voltage measurement, to ensure that for the capacitor-function of the skin does not decrease the accuracy of the measurement.

If during stimulation it is detected that a non-stimulated electrode has a comparable or even lower resistance as the (some of the) stimulation electrode(s), this non-stimulated electrode is added to the set of electrodes that are available for stimulation. It then depends on the actual stimulation strategy whether the new electrode is used for stimulation. For this invention, it is preferred that if the original stimulation electrode(s) lose their good connection to the skin, this newly discovered electrode can then be used to take over stimulation.

EMBODIMENT 4

Compensating for Changes in Resistance that Result from Stimulation of the Skin

Figure 13:
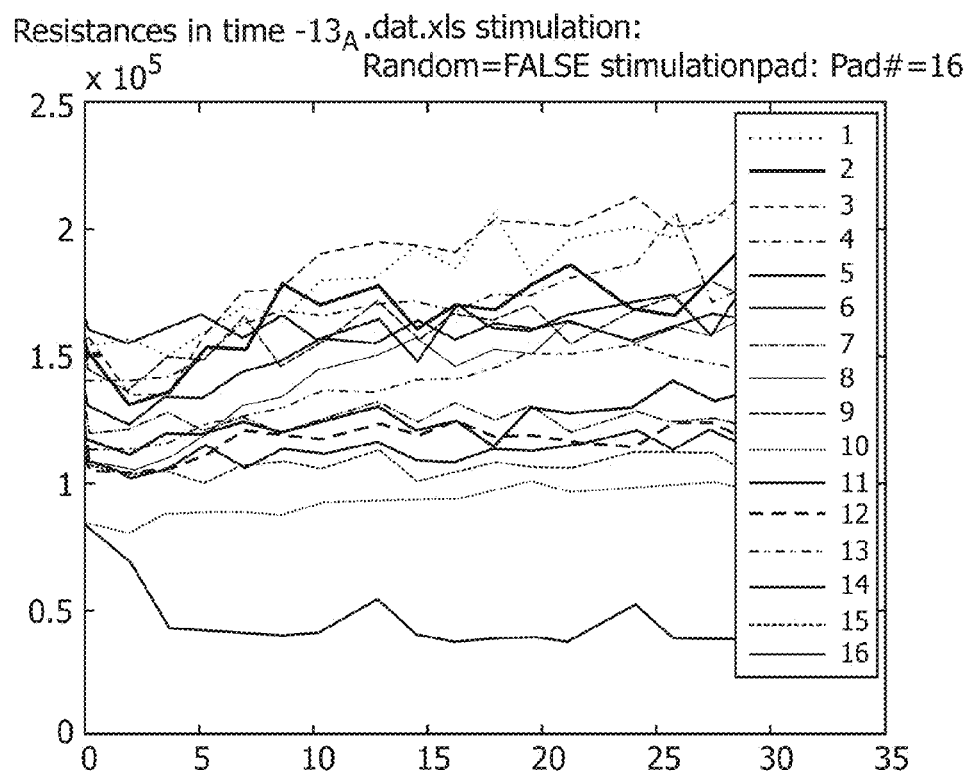
FIG. 13 shows evolution of measured resistance over time, the green line #2 (bottom) is the stimulated line.

FIG. 13 shows a typical evolution in time of measured resistances for a constellation of 16 electrodes. After an initial resistance measurement, the electrode with the lowest resistance is actively stimulated. Over a period of 2 to 5 minutes, the resistance typically drops significantly, in this example by 50%, while the resistance of non-stimulated electrodes typically does no drop as fast. In this example, the non-stimulated electrodes even increase their resistance.

The two advantages of this effect are that 1. if the electrodes shift over the skin, the large difference in resistance makes it easy to rediscover the previous stimulation point.

2. the number of electrodes that are used for stimulation can be reduced as the resistance drops (see above), making the stimulation more targeted.

FIG. 13. Evolution of measured resistance over time, the green line #2 (bottom) is the stimulated line.

However, the effect also has a disadvantage that has to be overcome

Figure 14:
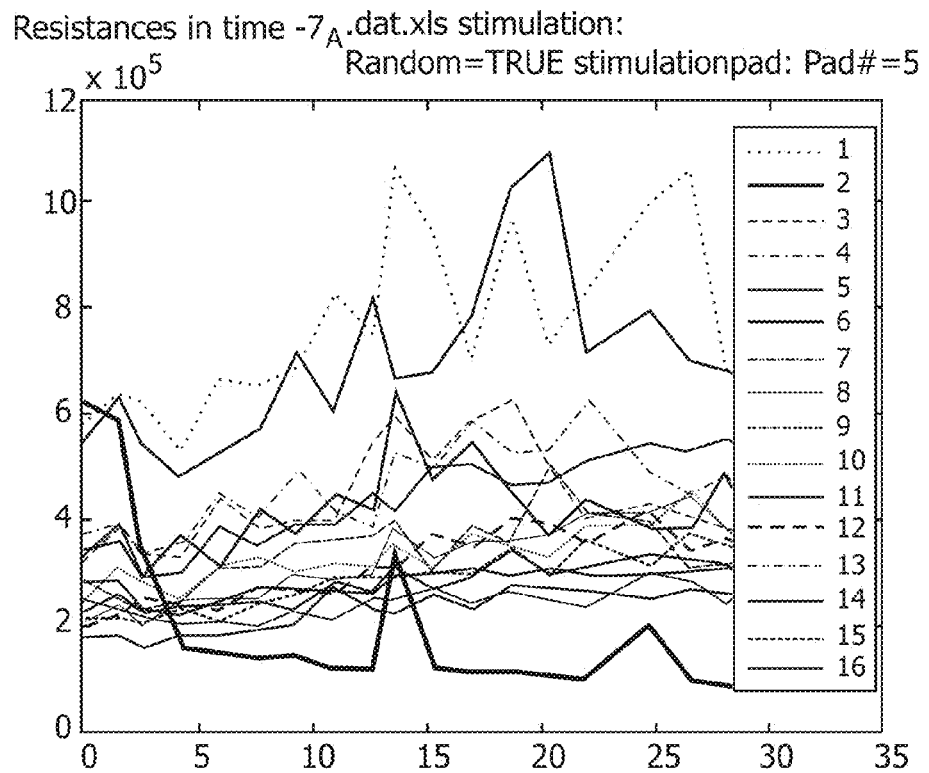
FIG. 14 shows stimulation of a high resistance electrode

FIG. 14. Stimulation of a High Resistance Electrode

FIG. 14 shows a stimulation trace where instead of the lowest resistance electrode; the highest resistance electrode is stimulated. Within 5 minutes of stimulation, its resistance has dropped by a factor 3, and the previously highest resistance electrode is now the lowest resistance electrode. Therefore, if due to temporary circumstances initially the best stimulation points were missed (e.g. temporary disconnect of the skin and the specific electrode pad), after 5 minutes the recalibration mechanism defined above will no longer select those best stimulation points.

To compensate for this effect the following mechanisms have been defined:

Mechanism 1: Pre-Stimulation

1. Initially stimulating all available electrodes for a limited duration (a maximum of 5 minutes suffices, but after 2.5 minutes the slope of the skin resistance improvement is also clear). This will result in a skin resistance drop for all points. Since resistance typically drops between 25% and a factor of 12, this can result in a different stimulation point having the lowest resistance.

2. Only at this time, select the actual stimulation points, based on a final resistance measurement.

Mechanism 2: Memory

1. Maintain for each electrode its stimulation history (between two levels) and its range of resistance measurements. This gives an average resistance pre-stimulation and post-stimulation, and a resistance change-speed. On determining a new stimulation point, consider for stimulated electrodes also their pre-stimulation resistance when comparing them with a non-stimulated electrode. If using this second metric a competitive electrode is found (e.g. measured resistance differs less then X %, where X is e.g. 20%), it can be stimulated for a limited duration (2 to 5 minutes) such that also their post-stimulation resistances can be compared.

2. Using the resistance change-speed it can be calculated whether a stimulated electrode has reached its lowest resistance, or whether its resistance is still decreasing. This is important as the time it takes to reach the lowest resistance varies from 2 minutes to 15 minutes depending on person and circumstances.

3. Select the electrode with a competitively low post-stimulation resistance that had the lowest resistance change factor.

The reason for this is that it has been identified that good stimulation points typically have a lower resistance improvement then poor stimulation points. The theory behind this is that good stimulation points have a free nerve end or nerve closer to the skin than poor stimulation points, and that stimulation of the skin improves its conductivity. Since for a good point there is less skin-tissue that can improve its conductivity, the improvement from stimulation is necessarily lower.

The embodiments of the present invention described herein are intended to be taken in an illustrative and not a limiting sense. Various modifications may be made to these embodiments by those skilled in the art without departing from the scope of the present invention as defined in the appended claims.

The invention claimed is:

1. A device for applying transcutaneous electrical nerve stimulation, the device comprising:
    a plurality of electrodes configured to stimulate nerves in a stimulation mode of operation and to detect resistance, one or more of the plurality of electrodes are configured as stimulation electrodes to stimulate nerves and different one or more of the plurality of electrodes are configured as non-stimulation electrodes to detect resistance;
    sensor configured to detect a change of a skin impedance; and
    a controller configured to switch from the stimulation mode of operation into a recalibration mode of operation upon detection of the changed skin impedance.

2. The device as claimed in claim 1, wherein the controller is configured to adjust an electrical current flowing through the skin via one or more of the plurality of electrodes.

3. The device as claimed in claim 2, wherein the controller is configured to adjust the electrical current during the recalibration mode of operation via:
    adapting a location of the electrode or of the plurality of electrodes for reducing the resistance of the electrode or of the plurality of electrodes or
    reapplying of the electrode or of the plurality of electrodes for reducing a resistance of the electrode or of the electrodes, or
    selecting a further electrode having reduced resistance from the plurality of electrodes for applying the transcutaneous electrical nerve stimulation, or
    selecting a third sub-set of electrodes from the plurality of electrodes for applying the transcutaneous electrical nerve stimulation simultaneously via the electrodes of the third sub-set of electrodes for reducing the resistance of the electrode or of the plurality of electrodes, or
    selecting a fourth sub-set of electrodes from the plurality of electrodes for applying the transcutaneous electrical nerve stimulation, the fourth sub-set of electrodes being chosen depending on local physiology, sensed resistance and user interaction.

4. The device as claimed in claim 3, wherein when adapting a location and/or re-applying the mode or the plurality of electrodes, the controller is configured to provide instructions to a user for adapting the location and/or reapplying the electrode or the plurality of electrodes.

5. The device as claimed in claim 1, wherein the changed skin impedance results in the switching of functioning of the device.

6. The device as claimed in claim 1, wherein the controller is configured to vary voltage per one or more of the plurality of electrodes to apply the transcutaneous electrical nerve stimulation.

7. The device as claimed in claim 6, further comprising a converter configured to generate a variation of the voltage in one or more of the plurality of electrodes.

8. The device as claimed in claim 6, wherein the changed skin impedance is detected
    via monitoring the voltage required for applying the transcutaneous electrical nerve stimulation at substantially constant current, and/or
    via monitoring a current resulting from applying the transcutaneous electrical new stimulation at substantially constant voltage, and/or
    via measuring a resistance of the electrode.

9. The device as claimed in claim 1, wherein in the stimulation mode of operation stimulation-voltage is used and wherein in the recalibration mode of operation measuring-voltage is used, the measuring-voltage is lower than the stimulation-voltage.

10. The device as claimed in claim 1, wherein
    the sensor detects the change of the skin impedance during the stimulation mode of operation,
    the resistance of at least one stimulation electrode of the plurality of electrodes is measured via monitoring the voltage for applying the transcutaneous electrical nerve stimulation, and
    the resistance of at least one non-stimulation electrode of the plurality of electrodes is measured via the measuring-voltage indicating the resistance of the electrode,
    the at least one stimulation electrode is configured for applying the transcutaneous electrical nerve stimulation, and
    the at least one non-stimulation electrode is configured for not applying the transcutaneous electrical nerve stimulation.

11. The device as claimed in claim 10, wherein the sensor is configured to measure the resistance of the non-stimulation electrodes during short breaks in the applying of the transcutaneous electrical nerve stimulation.

12. The device as claimed in claim 10, wherein the sensor is configured to measure the resistance of the stimulation electrodes of the plurality of electrodes for a first sub-set of electrodes.

13. The device as claimed in claim 10, wherein
    the controller is configured to apply a stimulation signal for stimulating the nerve to a second sub-set of electrodes of the plurality of electrodes during a predefined time-window, and
    the sensor is configured to monitor a resistance change of the electrodes of the second sub-set over time, and
    the controller is configured to select a specific electrode or a specific group of electrodes from the second sub-set in which the resistance change over time is below a predefined limit as the stimulation electrode or stimulation electrodes.

14. A method of transcutaneous electrical nerve stimulation comprising acts of:
    a device comprising a plurality of electrodes
    providing a plurality of electrodes for stimulating nerves in a stimulation mode of operation and for detecting resistance;
    dynamically adapting one or more of the plurality of electrodes as stimulation electrodes for stimulating nerves and different one or more of the plurality of electrodes as non-stimulation electrodes for detecting resistance;
    detecting a change of a skin impedance using non-stimulation electrodes, and
    switching from a stimulation mode of operation in which stimulation electrodes are used for stimulating the transcutaneous nerves into a recalibration mode of operation upon detection of the changed skin impedance.

15. The method as claimed in claim 14, wherein the dynamically adapting comprises acts selected from at least one of:
- adding neighboring of the plurality of electrodes having relatively low impedance to an existing stimulation electrode;
- adding neighboring of the plurality of electrodes within shortest distance from a relatively low impedance location to an existing stimulation electrode; and
- adding ones of the plurality of electrodes depending on known physiology of a body part to which the plurality of electrodes is applied.

* * * * *